(12) United States Patent
Kelly et al.

(10) Patent No.: US 6,602,862 B1
(45) Date of Patent: Aug. 5, 2003

(54) 1-AMINO-ALKYLCYCLOHEXANES AS TRYPANOCIDAL AGENTS

(75) Inventors: John M. Kelly, Hertfordshire (GB); Ivars Kalvinsh, Salaspils (LV); Valerjans Kauss; Aigars Jirgensons, both of Riga (LV); Markus Gold, Nauheim (DE)

(73) Assignee: Merz Pharma GmbH & Co., KGAA, Frankfurt am Main (DE)

( * ) Notice: Subject to any disclaimer, the term of this patent is extended or adjusted under 35 U.S.C. 154(b) by 25 days.

(21) Appl. No.: 09/664,629

(22) Filed: Sep. 19, 2000

(51) Int. Cl.$^7$ .................. A61K 31/33; A61K 31/13; A61K 31/16
(52) U.S. Cl. .................. 514/183; 514/579; 514/659
(58) Field of Search ................ 514/579, 659, 514/183

(56) References Cited

U.S. PATENT DOCUMENTS

| | | | |
|---|---|---|---|
| 5,516,806 A | | 5/1996 | Frei et al. |
| 6,034,134 A | | 3/2000 | Gold et al. |
| 6,071,966 A | * | 6/2000 | Gold et al. .................. 514/579 |
| 6,093,743 A | * | 7/2000 | Lai et al. .................... 514/599 |

OTHER PUBLICATIONS

John M. Kelly et al., "In vitro and in vivo activities of aminodamanatane and aminoalkylcyclohexane derivatives against Trypanosoma brucei", Antimicrob. Agents Chemother. (2001), 45(5), 1360–1366.

Y. Repetto et al., "Glutathione and trypanothione in several strains of Trypanosoma cruzi: Effect of drugs", Commparative Biochemistrya nd Physiology –B Biochemistry and Molecular Biology, (1996) 115/2 (281–285).

Alan J. Bitonti et al., "Characterization of spermidine synthase from Trypanosoma brucei brucei", Mol. Biochem. Parasitol (1984), 13(1), 21–28.

O.P. Shukla "Polyamine metabolism as a target for chemotherapy of parasitic infections" J. Sci. Ind. Res., (1990) 49(6), 263–282.

A.M. de Oliverira, "Structure–activity relationship of 110 candidate juvenille horome analogues for panstrongylus megistus (Burmeister 1835) a vector of Chagas Disease (Hemiptera Reduviidae, Triatominae)", Rev. Brasil. Biol., vol. 41, No. 1, Feb. 1981 (197–203).

S. Girault et al., "Structure–activity relationship in 2–aminodiphenylsulfides against trypanothione reductase from Trypanosoma cruzi", Bioorganic & Medicinal Chemistry Letters, Oxford, GB, vol. 8, No. 10, May 19, 1998, pp. 1175–1180.

* cited by examiner

Primary Examiner—Frederick Krass
Assistant Examiner—Donna Jagoe
(74) Attorney, Agent, or Firm—The Firm of Hueschen and Sage

(57) ABSTRACT

Certain 1-aminoalkylcyclohexanes are anti-trypanosomiasis agents and trypanocides. Pharmaceutical compositions thereof for such purpose and method of making same, as well as a method-of-treating trypanosomiasis therewith.

16 Claims, No Drawings

1-AMINO-ALKYLCYCLOHEXANES AS TRYPANOCIDAL AGENTS

FIELD OF INVENTION

New use of 1-amino-alkylcyclohexanes, i.e., as anti-parasitemial, anti-trypanosomiasis, or trypanocidal agents.

BACKGROUND OF THE INVENTION

Vector control and other public health measures have a successful history of containing African trypanosomiasis. However, war, civil unrest and economic problems have resulted in a breakdown of these interventions and the estimated annual incidence is now 300,000 cases. The causative agents of human trypanosomiasis are the tsetse fly-transmitted protozoan parasites *Trypanosoma brucei gambiense* (western and central Africa) and *Trypanosoma brucei rhodesiense* (eastern and southern Africa). In the bloodstream of infected individuals antigenic variation by the parasite prevents elimination by the immune system and the development of a vaccine is not considered feasible. The drugs used to treat trypanosomiasis are unsatisfactory. They all require hospitalization, are expensive, can fail to eradicate parasitemia and often have toxic side effects. Melarsoprol, which is used against the advanced stage of the disease that occurs once trypanosomes have invaded the central nervous system, causes 5 to 10% patient mortality due to arsenic encephalopathy. The only other drug available for clinical use against this stage of the disease, difluoromethylornithine (DFMO), has limited efficacy against *T.b. rhodesiense* infections and is very expensive. In the absence of treatment, trypanosomiasis is fatal and the development of new chemotherapeutic approaches is thus a priority.

PRIOR ART

The prior art is represented by our prior U.S. Pat. No. 6,034,134 of Mar. 7, 2000 and our published application WO 99/01416, PCT/EP98/04026, and Parsons et al. Neuropharmacology 38, 85–108 (1999), wherein the active compounds utilized according to the present invention are disclosed and disclosed to be NMDA receptor antagonists and anticonvulsants. We have subsequently disclosed them to be useful as 5HT$_3$ and neuronal nicotinic receptor antagonists.

THE PRESENT INVENTION

The present invention is directed to a new use of 1-amino-alkylcyclohexane compounds selected from the group consisting of those of the formula

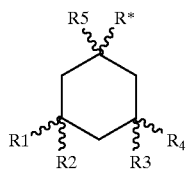

wherein R* is —(CH$_2$)$_n$—(CR$^6$R$^7$)$_m$—NR$^8$R$^9$
wherein n+m=0, 1, or 2
wherein R$^1$ through R$^7$ are independently selected from the group consisting of hydrogen and lower-alkyl (1–6C), and
wherein R$^8$ and R$^9$ each represent hydrogen or lower-alkyl (1–6C) or together represent lower-alkylene —(CH$_2$)$_x$— wherein x is 2 to 5, inclusive, and enantiomers, optical isomers, hydrates, and pharmaceutically-acceptable salts thereof, as well as pharmaceutical compositions thereof, and the preparation and use of such compounds and compositions for the treatment of a living animal as antitrypanosomiasis agents and as trypanocides.

Representative of these compounds are as follows:
MRZ 579: 1-Amino-1,3,3,5,5-pentamethylcyclohexane,
580: 3,3,5,5-Tetramethylcyclohexylmethylamine,
601: 1-Amino-1-propyl-3,3,5,5-tetramethylcyclohexane,
607: 1-Amino-1,3,3,5(trans)-tetramethylcyclohexane (axial amino group),
614: 3-Propyl-1,3,5,5-Tetramethylcyclohexylamine semihydrate (mixture of diastereomers ~1:2)
615: 1-Amino-1,3,5,5-tetramethyl-3-ethylcyclohexane (mixture of diastereomers),
616: 1-Amino-1,3,5-trimethylcyclohexane (mixture of diastereomers),
617: 1-Amino-1,3-dimethyl-3-propylcyclohexane (mixture of diastereomers),
618: 1-Amino-1,3 (trans),5 (trans)-trimethyl-3(cis)-propylcyclohexane,
620: 1-Amino-1,3-dimethyl-3-ethylcyclohexane,
621: 1-Amino-1,3,3-trimethylcyclohexane,
622: cis-3-Ethyl-1, trans-3, trans-5-trimethylcyclohexamine,
625: 1-Amino-1,3 (trans)-dimethylcyclohexane,
626: 1,3,3-Trimethyl-5,5-dipropylcyclohexylamine,
627: 1-Amino-1-methyl-3 (trans) propylcyclohexane,
628: 1-Methyl-3-cis-propylcyclohexylamine,
629: 1-Amino-1-methyl-3 (trans) ethylcyclohexane,
632: 1-Amino-1,3,3-trimethyl-5 (cis) ethylcyclohexane,
633: 1-Amino-1,3,3-trimethyl-5 (trans) ethylcyclohexane,
634: cis-3-Propyl-1,5,5-trimethylcyclohexylamine,
635: trans-3-Propyl-1,5,5-trimethylcyclohexylamine
639: N-Ethyl-1,3,3,5,5-pentamethylcyclohexylamine,
640: N-methyl-1-Amino-1,3,3,5.5-pentamethylcyclohexane,
641: 1-Amino-1-methylcyclohexane,
642: N,N-dimethyl-1-amino-1,3,3,5,5-pentamethylcyclohexane,
644: 2-(3,3,5,5-Tetramethylcyclohexyl)ethylamine,
645: 2-Methyl-1-(3,3,5,5-tetramethylcyclohexyl)propyl-2-amine,
662: 2-(1,3,3,5,5-Pentamethylcyclohexyl-1) ethylamine, semihydrate
705: N-(1,3,3,5,5-pentamethylcyclohexyl) pyrrolidine,
680: 1-amino-1,3(trans),5(trans)-trimethylcyclohexane,
681: 1-amino-1,3(cis),5(cis)-trimethylcyclohexane, .H$_2$O,
682: 1-amino-(1R,5S)trans-5-ethyl-1,3,3-trimethylcyclohexane,
683: 1-amino-(1S,5S)cis-5-ethyl-1,3,3-trimethylcyclohexane, .H$_2$O,
1-Amino-1,5,5-trimethyl-3(cis)-isopropyl-cyclohexane,
1-Amino-1,5,5-trimethyl-3(trans)-isopropyl-cyclohexane,
1-Amino-1-methyl-3 (cis)-ethyl-cyclohexane,
1-Amino-1-methyl-3(cis)-methyl-cyclohexane,
1-Amino-5,5-diethyl-1,3,3-trimethyl-cyclohexane, and
Also, 1-amino-1,3,3,5,5-pentamethylcyclohexane,
1-amino-1,5,5-trimethyl-3,3-diethylcyclohexane,
1-amino-1-ethyl-3,3,5,5-tetramethylcyclohexane,
N-ethyl-1-amino-1,3,3,5,5-pentamethylcyclohexane,
N-(1,3,5-trimethylcyclohexyl)pyrrolidine or piperidine,
N-[1,3(trans),5(trans)-trimethylcyclohexyl]pyrrolidine or piperidine,
N-[1,3(cis),5(cis)-trimethylcyclohexyl]pyrrolidine or piperidine, N-(1,3,3,5-tetramethylcyclohexyl)pyrrolidine or piperidine,
N-(1,3,3,5,5-pentamethylcyclohexyl)pyrrolidine or piperidine,
N-(1,3,5,5-tetramethyl-3-ethylcyclohexyl)pyrrolidine or piperidine,
N-(1,5,5-trimethyl-3,3-diethylcyclohexyl)pyrrolidine or piperidine,
N-(1,3,3-trimethyl-cis-5-ethylcyclohexyl)pyrrolidine or piperidine,
N-[(1S,5S)cis-5-ethyl-1,3,3-trimethylcyclohexyl] pyrrolidine or piperidine,
N-(1,3,3-trimethyl-trans-5-ethylcyclohexyl)pyrrolidine or piperidine,
N-[(1R,5S)trans-5-ethyl-1,3,3-trimethylcyclohexyl] pyrrolidine or piperidine,
N-(1-ethyl-3,3,5,5-tetramethylcyclohexyl)pyrrolidine or piperidine, and
N-(1-propyl-3,3,5,5-tetramethylcyclohexyl)pyrrolidine or piperidine,
and optical isomers, enantiomers, and the hydrochloride, hydrobromide, hydrochloride hydrate, or other pharmaceutically-acceptable salts of any of the foregoing.

Of particular interest are compounds of the foregoing formula wherein at least $R^1$, $R^4$, and $R^5$ are lower-alkyl and those compounds wherein $R^1$ through $R^5$ are methyl, those wherein x is 4 or 5, and in particular the compound N-(1,3,3,5,5-pentamethylcyclohexyl) pyrrolidine, and optical isomers, enantiomers, hydrates and pharmaceutically-acceptable salts thereof.

In our U.S. Pat. No. 6,034,134 of Mar. 7, 2000, we disclosed compounds of the foregoing formula, pharmaceutical compositions thereof, and their use as NMDA-receptor antagonists and anticonvulsants. It has now been found that compounds of the foregoing formula and optical isomers, enantiomers, hydrates and pharmaceutically-acceptable salts thereof, in addition to their NMDA antagonist and anticonvulsant properties, quite unpredictably possess a high degree of anti-trypanosomiasis activity, making them useful in the treatment of trypanosomiasis and as trypanocides.

SUMMARY OF THE INVENTION

What we therefore believe to be comprised by our present invention may be summarized, inter alia, in the following words:

A method-of-treating a living animal for inhibition of progression or alleviation of a condition which is alleviated by an anti-trypanosomiasis agent or trypanocide, comprising the step of administering to the said living animal an amount of a 1-aminoalkylcyclohexane compound selected from the group consisting of those of the formula

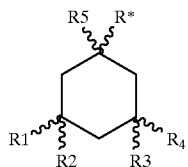

wherein R* is —$(CH_2)_n$—$(CR^6R^7)_m$—$NR^8R^9$
wherein n+m=0, 1, or 2
wherein $R^1$ through $R^7$ are independently selected from the group consisting of hydrogen and lower-alkyl (1–6C),
wherein $R^8$ and $R^9$ are independently selected from the group consisting of hydrogen and lower-alkyl (1–6C) or together represent lower-alkylene —$(CH_2)_x$— wherein x is 2 to 5, inclusive, and optical isomers, enantiomers, hydrates, and pharmaceutically-acceptable salts thereof, which is effective for the said purpose; such a
method wherein at least $R^1$, $R^4$, and $R^5$ are lower-alkyl; such a
  method wherein $R^1$ through $R^5$ are methyl; such a
  method wherein $R^1$ is ethyl; such a
  method wherein $R^2$ is ethyl; such a
  method wherein $R^3$ is ethyl; such a
  method wherein $R^4$ is ethyl; such a
  method wherein $R^5$ is ethyl; such a
  method wherein $R^5$ is propyl; such a
  method wherein $R^6$ or $R^7$ is methyl; such a
  method wherein $R^6$ or $R^7$ is ethyl; such a
  method wherein X is 4 or 5; such a
  method wherein the compound is selected from the group consisting of
    580: 3,3,5,5-Tetramethylcyclohexylmethylamine,
    601: 1-Amino-1-propyl-3,3,5,5-tetramethylcyclohexane,
    607: 1-Amino-1,3,3,5(trans)-tetramethylcyclohexane (axial amino group),
    614: 3-Propyl-1,3,5,5-tetramethylcyclohexylamine semihydrate (mixture of diastereomers ~1:2)
    615: 1-Amino-1,3,5,5-tetramethyl-3-ethylcyclohexane (mixture of diastereomers),
    617: 1-Amino-1,3-dimethyl-3-propylcyclohexane (mixture of diastereomers),
    618: 1-Amino-1,3 (trans),5 (trans)-trimethyl-3 (cis)-propylcyclohexane,
    620: 1-Amino-1,3-dimethyl-3-ethylcyclohexane,
    621: 1-Amino-1,3,3-trimethylcyclohexane,
    622: cis-3-Ethyl-1, trans-3, trans-5-trimethylcyclohexamine,
    625: 1-Amino-1,3 (trans)-dimethylcyclohexane,
    626: 1,3,3-Trimethyl-5,5-dipropylcyclohexylamine,
    627: 1-Amino-1-methyl-3 (trans) propylcyclohexane,
    628: 1-Methyl-3-cis-propylcyclohexylamine,
    629: 1-Amino-1-methyl-3 (trans) ethylcyclohexane,
    632: 1-Amino-1,3,3-trimethyl-5 (cis) ethylcyclohexane,
    633: 1-Amino-1,3,3-trimethyl-5 (trans) ethylcyclohexane,
    634: cis-3-Propyl-1,5,5-trimethylcyclohexylamine,
    635: trans-3-Propyl-1,5,5-trimethylcyclohexylamine,
    639: N-Ethyl-1,3,3,5,5-pentamethylcyclohexylamine,
    641: 1-Amino-1-methylcyclohexane,
    642: N,N-dimethyl-1-amino-1,3,3,5,5-pentamethylcyclohexane,
    644: 2-(3,3,5,5-Tetramethylcyclohexyl) ethylamine,
    645: 2-Methyl-1-(3,3,5,5-tetramethylcyclohexyl) propyl-2-amine,
    662: 2-(1,3,3,5,5-Pentamethylcyclohexyl-1) ethylamine, semihydrate,
and optical isomers, enantiomers, hydrates and pharmaceutically-acceptable salts of any of the foregoing; and such a method wherein the compound is administered in the form of a pharmaceutical composition thereof comprising the compound in combination with one or more pharmaceutically-acceptable diluents, excipients, or carriers.

Moreover, the use of a 1-aminoalkylcyclohexane selected from the group consisting of those of the formula

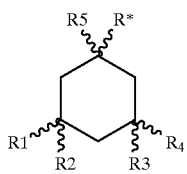

wherein R* is —(CH$_2$)$_n$—(CR$^6$R$^7$)$_m$—NR$^8$R$^9$
wherein n+m=0, 1, or 2
wherein R$^1$ through R$^7$ are independently selected from the group consisting of hydrogen and lower-alkyl (1–6C), wherein R$^8$ and R$^9$ are independently selected from the group consisting of hydrogen and lower-alkyl or together represent lower-alkylene —(CH$_2$)$_x$— wherein x is 2 to 5, inclusive, and optical isomers, enantiomers, hydrates, and pharmaceutically-acceptable salts thereof, in the manufacture of a medicament to treat a living animal for alleviation or elimination of trypanosomiasis; such a use wherein at least R$^1$, R$^4$, and R$^5$ are lower-alkyl; such a
use wherein R$^1$ through R$^5$ are methyl; such a
use wherein x is 4 or 5; such a
use wherein the compound is selected from the group consisting of
  580: 3,3,5,5-Tetramethylcyclohexylmethylamine,
  601: 1-Amino-1-propyl-3,3,5,5-tetramethylcyclohexane,
  607: 1-Amino-1,3,3,5(trans)-tetramethylcyclohexane (axial amino group),
  614: 3-Propyl-1,3,5,5-tetramethylcyclohexylamine semihydrate (mixture of diastereomers ~1:2)
  615: 1-Amino-1,3,5,5-tetramethyl-3-ethylcyclohexane (mixture of diastereomers),
  617: 1-Amino-1,3-dimethyl-3-propylcyclohexane (mixture of diastereomers),
  618: 1-Amino-1,3 (trans),5 (trans)-trimethyl-3 (cis)-propylcyclohexane,
  620: 1-Amino-1,3-dimethyl-3-ethylcyclohexane,
  621: 1-Amino-1,3,3-trimethylcyclohexane,
  622: cis-3-Ethyl-1, trans-3, trans-5-trimethylcyclohexamine,
  625: 1-Amino-1,3 (trans)-dimethylcyclohexane,
  626: 1,3,3-Trimethyl-5,5-dipropylcyclohexylamine,
  627: 1-Amino-1-methyl-3 (trans) propylcyclohexane,
  628: 1-Methyl-3-cis-propylcyclohexane,
  629: 1-Amino-1-methyl-3 (trans) ethylcyclohexane,
  632: 1-Amino-1,3,3-trimethyl-5 (cis) ethylcyclohexane,
  633: 1-Amino-1,3,3-trimethyl-5 (trans) ethylcyclohexane,
  634: cis-3-Propyl-1,5,5-trimethylcyclohexylamine,
  635: trans-3-Propyl-1,5,5-trimethylcyclohexylamine,
  639: N-Ethyl-1,3,3,5,5-pentamethylcyclohexylamine,
  641: 1-Amino-1-methylcyclohexane,
  642: N,N-dimethyl-1-amino-1,3,3,5,5-pentamethylcyclohexane, .H$_2$O
  644: 2-(3,3,5,5-Tetramethylcyclohexyl) ethylamine,
  645: 2-Methyl-1-(3,3,5,5-tetramethylcyclohexyl) propyl-2-amine,
  662: 2-(1,3,3,5,5-Pentamethylcyclohexyl-1) ethylamine, semihydrate,
and optical isomers, enantiomers, hydrates and pharmaceutically-acceptable salts of any of the foregoing.

THE PRESENT INVENTION IN DETAIL
Background and Pharmacoloqy

Some of us reported recently that the bloodstream form of the African trypanosome, *Trypanosoma brucei*, is sensitive to the anti-influenza virus drug rimantadine. In this patent application, we describe the trypanocidal properties of aminoalkylcyclohexane derivatives. Six of the compounds were found to inhibit growth in vitro of bloodstream form *T. brucei* by greater than 90% at concentrations in the range 0.3–0.7 μg ml$^{-1}$. A correlation between structural features of the derivatives and their trypanocidal properties was observed; hydrophobic substitutions generally enhanced activity.

METHODS
Synthesis

The synthesis of the novel amino-alkylcyclohexanes which are utilized according to the present invention has been described in U.S. Pat. No. 6,034,134 of Mar. 7, 2000.
Alternative Procedure The 1-cyclic amino compounds may also be prepared by reacting the corresponding 1-free amino-alkylcyclohexane and the selected alpha, omega-dihaloalkyl compound, e.g., 1,3-dibromopropane, 1,4-dibromobutane, or 1,5-dibromopentane, according to the following representative example:
N-(1,3,3,5,5-Pentamethylcvclohexyl)pyrrolidine Hydrochloride 1,3,3,5,5-pentamethylcyclohexylamine hydrochloride (12 g, 58.3 mmol), potassium carbonate (48.4 g, 350 mmol) and 1,4-dibromobutane (7.32 ml, 61.3 mmol) were refluxed in acetonitrile (250 ml) for 60 h. After cooling to r.t., the mixture was filtered and the precipitate was washed with diethyl ether (600 ml). The filtrate was concentrated in vacuo by rotary evaporation and the residue was fractionally distilled at reduced pressure (11 mm/Hg). The fraction at 129° C. was collected to obtain colorless oil (8.95 g). This was dissolved in diethyl ether (120 ml) and 2.7 M HCl solution in diethyl ether (30 ml) was added. The resulting precipitate was filtered off, washed with diethyl ether (3*30 ml) and dried in vacuo over NaOH to give N-(1,3,3,5,5-pentamethylcyclohexyl) pyrrolidine hydrochloride hydrate (12.9 g, 68%) with m.p. 158° C. PMR spectrum: (DMSO-d6, TMS) d: 0.97 (6H, s, 3,5-CH3); 1.11 (6H,s, 3,5-CH3); 0.8–1.4 (2H, cyclohexane 4-CH2) 1.41 (3H, s, 1-CH3); 1.69 (4H, m, cyclohexane 2,6-CH2); 1.84 (4H, m, pyrrolidine 3,4-CH2); 3.20 (4H, m, pyrrolidine 2,5-CH2); 10.9 ppm (1H, br s, NH+). Elemental analysis (C15H29n*HCl*H20) Found (%) C 65.0; H 11.7; N5.0 Calculated (%) C 64.8; H 11.6; N 5.0.
Parasites and Drug Testing in vitro Bloodstream form T-brucei (strain 427) were cultured in 25 cm$^3$ flasks at 37° C. in modified Iscove's medium (pH 7.4). To establish the extent of trypanocidal activity, parasites were grown for three days in the presence of test compounds (aminoalkylcyclohexane derivatives) and the concentrations which inhibited growth by 50%($IC_{50}$) and 90%($IC_{90}$) were determined. In these experiments, which were performed at least in triplicate, the density of untreated cultures increased from $0.25 \times 10^5$ cells $ml^{-1}$ to $4 \times 10^6$ cells $ml^{-1}$. After determination of cell densities at each drug concentration using a hemocytometer (Weber Scientific International Ltd), drug sensitivity was expressed as a percentage of growth of control cells.

Results

Table A shows the general structure of selected amino-alkylcyclohexanes used in the present study.

TABLE A

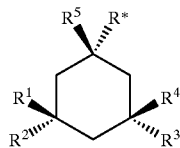

| MRZ | R1 | R2 | R3 | R4 | R5 | R* |
|---|---|---|---|---|---|---|
| | | | Basic Structure of the Amino-alkylcyclohexanes | | | |
| 601 | $CH_3$ | $CH_3$ | $CH_3$ | $CH_3$ | $C_3H_7$ | $NH_2$ |
| 607 | $CH_3$ | $CH_3$ | H | $CH_3$ | $C_3H_7$ | $NH_2$ |
| 615 | $CH_3$ | $CH_3$ | $C_2H_5(CH_3)$ | $CH_3(C_2H_5)$ | $CH_3$ | $NH_2$ |
| 617 | H | H | $CH_3(C_3H_7)$ | $C_3H_7(CH_3)$ | $CH_3$ | $NH_2$ |
| 618 | $CH_3$ | H | $C_3H_7$ | $CH_3$ | $CH_3$ | $NH_2$ |
| 620 | H | H | $C_2H_5(CH_3)$ | $CH_3(C_2H_5)$ | $CH_3$ | $NH_2$ |
| 621 | H | H | $CH_3$ | $CH_3$ | $CH_3$ | $NH_2$ |
| 627 | H | H | H | $C_3H_7$ | $CH_3$ | $NH_2$ |
| 629 | H | H | H | $C_2H_5$ | $CH_3$ | $NH_2$ |
| 632 | $CH_3$ | $CH_3$ | $C_2H_5$ | H | $CH_3$ | $NH_2$ |
| 633 | $CH_3$ | $CH_3$ | H | $C_2H_5$ | $CH_3$ | $NH_2$ |
| 641 | H | H | H | H | $CH_3$ | $NH_2$ |
| 642 | $CH_3$ | $CH_3$ | $CH_3$ | $CH_3$ | $CH_3$ | $NH(CH_3)_2$ |

Substitutions in brackets represent alternatives in racemic mixtures, e.g., $CH_3(C_3H_7)$ means $CH_3$ or $C_3H_7$.

Testing in vitro

In a preliminary screen, bloodstream form T.brucei were cultured for 3 days in growth medium at pH 7.4 in the presence of aminoalkylcyclohexane derivatives at a concentration of 5 $\mu g$ $ml^{-1}$. A range of activities was observed with the compounds tested. The compounds which inhibited growth by 90% or greater were then tested further to determine their $IC_{50}$s and $IC_{90}$s. Several of the compounds were found to have appreciable trypanocidal activity. In some cases, this was more than 10 times greater than had previously been observed with α-methyl-1-adamantane methylamine.

The effects of a number of aminoalkylcyclohexane derivatives on cultured bloodstream form T.brucei were investigated. The three most active of these compounds share structural similarities with each other, having amino-ethyl (662 and 644—cf. Table 1) or aminomethylpropyl (645—cf. Table 1) groups attached to the cyclohexane ring at position 1. They also have dimethyl substitutions at the 3 and 5 positions, a feature present in other derivatives (580, 601 and 639—cf. Table 1) found to have an $IC_{90}$ of less than 2 $\mu g$ $ml^{-1}$. It can also be seen from our data that the presence of dipropyl side chains, as in compound 626 (cf. Table 1), greatly increases the trypanocidal activity.

Discussion

The pharmacological activity of aminoalkylcyclohexane derivatives is representatively identified in Table 1.

An essential requirement for trypanocidal activity in the alkylcyclohexane derivatives is possession of an amino group. This can be attached directly to the cyclohexane ring or be attached via a side chain at the 1 position. Compounds in which the amino group is attached only to a cyclohexane ring also exhibited considerable toxicity to trypanosomes. See Table 1.

The trypanocidal properties of aminoalkylcyclohexane compounds were enhanced by the addition of a bulky side group at position 3. A cyclohexane ring suggests that increased hydrophobicity may be an important factor in determining the activity. There was a significant correlation between hydrophobicity and trypanocidal activity with aminoalkylcyclohexanes (compare compounds 626 and 620; Table 1).

The Table Representative Results

Table 1 Cultured bloodstream form T. brucci were incubated at 37° for 3 days in the presence of aminoalkylcyclohexane derivatives. Initially each compound was screened to determine the inhibitory effect at 5 $\mu g$ $ml^{-1}$ (data in brackets). For the more active compounds, the concentrations that inhibited growth by 50% and 90% were then evaluated. Each experiment was performed in triplicate, except where indicated (++). These data were obtained from six experiments. Values are presented as ±SD from the mean. Where stock compounds (20 mg $ml^{-1}$) were dissolved in DMSO that are indicated as (*) and (#) indicates that they were dissolved in 50:50 (v/v) $EtOH:H_2O$. All other compounds were dissolved in $H_2O$. Control cells were treated accordingly. ND stands for not done.

TABLE 1

| COMPOUND | $IC_{50}$ ($\mu g$ $ml^{-1}$) | $IC_{90}$ ($\mu g$ ml–1) | (Inhibition) (5 $\mu g$ $ml^{-1}$) |
|---|---|---|---|
| 625 | ND | ND | (0%) |
| 629 | ND | ND | (2%) |
| 607 | ND | ND | (17%) |
| 627 | ND | ND | (17%) |
| 642 | ND | ND | (21%) |
| 620 | ND | ND | (25%) |
| 621 | ND | ND | (40%) |
| 622 | ND | ND | (40%) |
| 633 | ND | ND | (68%) |
| 641 | ND | ND | (86%) |
| 632 | 2.92 ± 0.19 | 3.80 ± 0.07 | |
| 635 | 2.23 ± 0.33 | 3.67 ± 0.06 | |
| 618 | 2.19 ± 0.69 | 3.59 ± 0.17 | |
| 617 | 1.54 ± 0.08 | 2.33 ± 0.24 | |
| 628 | 1.54 ± 0.02 | 1.95 ± 0.03 | |
| 615 | 1.45 ± 0.07 | 1.93 ± 0.02 | |
| 580 | 1.44 ± 0.09 | 1.89 ± 0.02 | |
| 601 | 1.43 ± 0.08 | 1.87 ± 0.02 | |
| 639 | 1.37 ± 0.19 | 1.96 ± 0.03 | |
| 634 | 0.57 ± 0.13 | 0.77 ± 0.15++ | |
| 614 | 0.55 ± 0.11 | 0.88 ± 0.09++ | |
| *626 | 0.25 ± 0.01 | 0.29 ± 0.01 | |
| 662 | 0.24 ± 0.03 | 0.38 ± 0.08++ | |
| 644 | 0.23 ± 0.02 | 0.31 ± 0.03 | |
| *645 | 0.22 ± 0.02 | 0.29 ± 0.01 | |

PHARMACEUTICAL COMPOSITIONS

The active anti-trypanosomiasis agents of the invention, together with one or more conventional adjuvants, carriers, or diluents, may be placed into the form of pharmaceutical compositions and unit dosages thereof, and in such form may be employed as solids, such as coated or uncoated tablets or filled capsules, or liquids, such as solutions, suspensions, emulsions, elixirs, or capsules filled with the same, all for oral use; in the form of suppositories or capsules for rectal administration or in the form of sterile injectable solutions for parenteral (including intravenous or subcutaneous) use. Such pharmaceutical compositions and unit dosage forms thereof may comprise conventional or new ingredients in conventional or special proportions, with or without additional active compounds or principles, and such unit dosage forms may contain any suitable effective amount of the active ingredient commensurate with the intended daily dosage range to be employed. Tablets containing twenty (20) to one hundred (100) milligrams of active ingredient or, more broadly, ten (10) to two hundred fifty (250) milligrams per tablet, are accordingly representative unit dosage forms.

METHOD OF TREATING

Due to their high degree of anti-trypanosomiasis activity and their relatively low toxicity, together presenting a favorable therapeutic index, the active principles of the invention may be administered to a subject, e.g., a living animal (including a human) body, in need thereof, for the treatment, alleviation, or amelioration, palliation, or elimination of an indication or condition which is susceptible thereto, or representatively of an indication or condition set forth elsewhere in this application, preferably concurrently, simultaneously, or together with one or more pharmaceutically-acceptable excipients, carriers, or diluents, especially and preferably in the form of a pharmaceutical composition thereof, whether by oral, rectal, or parental (including intravenous and subcutaneous) or in some cases even topical route, in an effective amount. Dosage ranges may be 1–1000 milligrams daily, preferably 10–500 milligrams daily, and especially 50–500 milligrams daily, depending as usual upon the exact mode of administration, form in which administered, the indication toward which the administration is directed, the subject involved and the body weight of the subject involved, and the preference and experience of the physician or veterinarian in charge.

EXAMPLES OF REPRESENTATIVE PHARMACEUTICAL COMPOSITIONS

With the aid of commonly used solvents, auxiliary agents and carriers, the reaction products can be processed into tablets, coated tablets, capsules, drip solutions, suppositories, injection and infusion preparations, and the like and can be therapeutically applied by the oral, rectal, parenteral, and additional routes. Representative pharmaceutical compositions follow.

(a) Tablets suitable for oral administration which contain the active ingredient may be prepared by conventional tabletting techniques.

(b) For suppositories, any usual suppository base may be employed for incorporation thereinto by usual procedure of the active ingredient, such as a polyethyleneglycol which is a solid at normal room temperature but which melts at or about body temperature.

(c) For parental (including intravenous and subcutaneous) sterile solutions, the active ingredient together with conventional ingredients in usual amounts are employed, such as for example sodium chloride and double-distilled water q.s., according to conventional procedure, such as filtration, aseptic filling into ampoules or IV-drip bottles, and autoclaving for sterility.

Other suitable pharmaceutical compositions will be immediately apparent to one skilled in the art.

The following examples are given by way of illustration only and are not to be construed as limiting.

EXAMPLE 1

Tablet Formulation

A suitable formulation for a tablet containing 10 milligrams of active ingredient is as follows:

|  | Mg. |
| --- | --- |
| Active Ingredient | 10 |
| Lactose | 63 |
| Microcrystalline Cellulose | 21 |
| Talcum | 4 |
| Magnesium stearate | 1 |
| Colloidal silicon dioxide | 1 |

EXAMPLE 2

Tablet Formulation

Another suitable formulation for a tablet containing 100 mg is as follows:

|  | Mg. |
| --- | --- |
| Active Ingredient | 100 |
| Potato starch | 20 |
| Polyvinylpyrrolidone | 10 |
| Film coated and colored. | |
| The film coating material consists of: | |
| Lactose | 100 |
| Microcryst. Cellulose | 80 |
| Gelatin | 10 |
| Polyvinylpyrrolidone, crosslinked | 10 |
| Talcum | 10 |
| Magnesium stearate | 2 |
| Colloidal silicon dioxide | 3 |
| Color pigments | 5 |

EXAMPLE 3

Capsule Formulation A suitable formulation for a capsule containing 50 milligrams of active ingredient is as follows:

|  | Mg. |
| --- | --- |
| Active Ingredient | 50 |
| Corn starch | 20 |
| Dibasic calcium phosphate | 50 |
| Talcum | 2 |
| Colloidal silicon dioxide | 2 | filled in a gelatin capsule.

EXAMPLE 4

Solution for Injection

A suitable formulation for an injectable solution containing one percent of active ingredient is as follows:

| Active Ingredient mg | 12 |
|---|---|
| Sodium chloride mg | 8 |
| Sterile water to make ml | 1 |

EXAMPLE 5

Liquid Oral Formulation

A suitable formulation for 1 liter of a liquid mixture containing 2 milligrams of active ingredient in one milliliter of the mixture is as follows:

| | G. |
|---|---|
| Active Ingredient | 2 |
| Saccharose | 250 |
| Glucose | 300 |
| Sorbitol | 150 |
| Orange flavor | 10 |
| Sunset yellow. | |
| Purified water to make a total of 1000 ml | |

EXAMPLE 6

Liquid Oral Formulation

Another suitable formulation for 1 liter of a liquid mixture containing 20 milligrams of active ingredient in one milliliter of the mixture is as follows:

| | G. |
|---|---|
| Active Ingredient | 20 |
| Tragacanth | 7 |
| Glycerol | 50 |
| Saccharose | 400 |
| Methylparaben | 0.5 |
| Propylparaben | 0.05 |
| Black currant-flavor | 10 |
| Soluble Red color | 0.02 |
| Purified water to make a total of 1000 ml. | |

EXAMPLE 7

Liquid Oral Formulation

Another suitable formulation for 1 liter of a liquid mixture containing 2 milligrams of active ingredient in one milliliter of the mixture is as follows:

| | G. |
|---|---|
| Active Ingredient | 2 |
| Saccharose | 400 |
| Bitter orange peel tincture | 20 |
| Sweet orange peel tincture | 15 |
| Purified water to make a total of 1000 ml. | |

EXAMPLE 8

Aerosol Formulation 180 g aerosol solution contain:

| | G. |
|---|---|
| Active Ingredient | 10 |
| Oleic acid | 5 |
| Ethanol | 81 |
| Purified Water | 9 |
| Tetrafluoroethane | 75 |

15 ml of the solution are filled into aluminum aerosol cans, capped with a dosing valve, purged with 3.0 bar.

EXAMPLE 9

TDS Formulation 100 g solution contain:

| | G. |
|---|---|
| Active Ingredient | 10.0 |
| Ethanol | 57.5 |
| Propyleneglycol | 7.5 |
| Dimethylsulfoxide | 5.0 |
| Hydroxyethylcellulose | 0.4 |
| Purified water | 19.6 |

1.8 ml of the solution are placed on a fleece covered by an adhesive backing foil. The system is closed by a protective liner which will be removed before use.

EXAMPLE 10

Nanoparticle Formulation 10 g of polybutylcyanoacrylate nanoparticles contain:

| | G. |
|---|---|
| Active Ingredient | 1.0 |
| Poloxamer | 0.1 |
| Butylcyanoacrylate | 8.75 |
| Mannitol | 0.1 |
| Sodiumchloride | 0.05 |

Polybutylcyanoacrylate nanoparticles are prepared by emulsion polymerization in a water/0.1 N HCl/ethanol mixture as polymerization medium. The nanoparticles in the suspension are finally lyophilized under vacuum.

The compounds of the invention thus find application in the treatment of a living animal body, especially a human, for parasitemia such as trypanosomiasis or as trypanocidal agents.

The method-of-treating a living animal body with a compound of the invention, for the inhibition of progression or alleviation of the selected ailment therein, is as previously stated by any normally-accepted pharmaceutical route, employing the selected dosage which is effective in the alleviation of the particular ailment desired to be alleviated.

Use of the compounds of the present invention in the manufacture of a medicament for the treatment of a living animal for inhibition of progression or alleviation of the selected ailment or condition, particularly for parasitemia such as trypanosomiasis or as trypanocidal agents, is carried out in the usual manner comprising the step of admixing an effective amount of a compound of the invention with a pharmaceutically-acceptable diluent, excipient, or carrier, and the method-of-treating, pharmaceutical compositions, and use of a compound of the present invention in the manufacture of a medicament are all in accord with the foregoing and with the disclosure of our prior U.S. Pat. No. 6,034,134 for the same 1-amino compounds, and representative acid addition salts, enantiomers, isomers, and hydrates, and their method of preparation is likewise disclosed in our prior USP and published WO application for the 1-amino-alkylcyclohexane compounds.

Representative pharmaceutical compositions are prepared by admixing the active anti-trypanosomiasis ingredient with a suitable pharmaceutically-acceptable excipient, diluent, or carrier, include tablets, capsules, solutions for injection, liquid oral formulations, aerosol formulations, TDS formulations, and nanoparticle formulations, thus to produce medicaments for oral, injectable, or dermal use, also in accord with the foregoing and also in accord with examples of pharmaceutical compositions given in our U.S. Pat. No. 6,034,134 for these 1-amino-alkylcyclohexanes.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can be legally accorded to the appended claims.

We claim:

1. A method-of-treating a living animal for inhibition of progression or alleviation of a condition which is alleviated by an anti-trypanosomiasis agent or by a trypanocide, comprising the step of administering to the said living animal an amount of a 1-aminoalkylcyclohexane compound selected from the group consisting of those of the formula

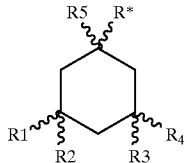

wherein R* is —(CH$_2$)$_n$—(CR$^6$R$^7$)$_m$—NR$^8$R$^9$
wherein n+m=0, 1, or 2
wherein R$^1$ through R$^7$ are independently selected from the group consisting of hydrogen and lower-alkyl (1–6C),
wherein R$^8$ and R$^9$ are independently selected from the group consisting of hydrogen and lower-alkyl (1–6C) or together represent lower-alkylene —(CH$_2$)$_x$— wherein x is 2 to 5, inclusive, and optical isomers, enantiomers, hydrates, and pharmaceutically-acceptable salts thereof, which is effective for the said purpose.

2. A method of claim 1 wherein at least R$^1$, R$^4$, and R$^5$ are lower-alkyl.

3. A method of claim 2 wherein R$^1$ through R$^5$ are methyl.

4. A method of claim 3 wherein X is 4 or 5.
5. A method of claim 2 wherein X is 4 or 5.
6. A method of claim 1 wherein R$^1$ is ethyl.
7. A method of claim 1 wherein R$^2$ is ethyl.
8. A method of claim 1 wherein R$^3$ is ethyl.
9. A method of claim 1 wherein R$^4$ is ethyl.
10. A method of claim 1 wherein R$^5$ is ethyl.
11. A method of claim 1 wherein R$^5$ is propyl.
12. A method of claim 1 wherein R$^6$ or R$^7$ is methyl.
13. A method of claim 1 wherein R$^6$ or R$^7$ is ethyl.
14. A method of claim 1 wherein the compound is selected from the group consisting of 3,3,5-Tetraetthylcyclohexylmethyl amine,
1-Amino-1-propyl-3,3,5,5-tetramethylcyclohexane,
1-Amino-1,3,3,5 (trans)-tetramethylcyclohexane (axial amino group),
3-Propyl-1,3,5,5-tetramethylcyclohexylamine semihydrate (mixture of diastereomers ~1:2)
1-Amino-1,3,5,5-tetramethyl-3-ethylcyclohexane (mixture of diastereomers),
1-Amino-1,3-dimethyl-3-propylcyclohexane (mixture of diastereomers),
1-Amino-1,3 (trans),5 (trans)-trimethyl-3(cis)-propylcyclohexane,
1-Amino-1,3-dimethyl-3-ethylcyclohexane,
1-Amino-1,3,3-trimethylcyclohexane,
cis-3-Ethyl-1, trans-3, trans-5-trimethylcyclohex-amine,
1,3,3-Trimethyl-5,5-dipropylcyclohexylamine,
1-Amino-1-methyl-3 (trans) propylcyclohexane,
1-Methyl-3-cis-propylcyclohexylamine,
1-Amino-1-methyl-3 (trans) ethylcyclohexane,
1-Amino-1,3,3-trimethyl-5 (cis) ethylcyclohexane,
1-Amino-1,3,3-trimethyl-5 (trans) ethylcyclohexane,
cis-3-Propy-1,5,5-trimethylcyclohexylamine,
trans-3-Propyl-1,5,5-trimethylcyclohexylamine,
N-Ethyl-1,3,3,5,5-pentamethylcyclohexylamine,
1-Amino-1-methylcyclohexane,
N,N-dimethyl-1-amino-1,3,3,5,5-pentamethylcyclohexane,
2-(3,3,5,5-Tetramethylcyclohexyl)ethylamine,
2-Methyl-1-(3,3,5,5-tetramethylcyclohexyl)propyl-2-amine,
2-(1,3,3,5,5-Pentamethylcyclohexyl-1) ethylamine, semihydrate,
and optical isomers, enantiomers, hydrates and pharmaceutically-acceptable salts of any of the foregoing.

15. A method of claim 14 wherein the compound is administered in the form of a pharmaceutical composition thereof comprising the compound in combination with one or more pharmaceutically-acceptable diluents, excipients, or carriers.

16. A method of claim 1 wherein the compound is administered in the form of a pharmaceutical composition thereof comprising the compound in combination with one or more pharmaceutically-acceptable diluents, excipients, or carriers.

* * * * *

UNITED STATES PATENT AND TRADEMARK OFFICE
CERTIFICATE OF CORRECTION

PATENT NO. : 6,602,862 B1
APPLICATION NO. : 09/664629
DATED : August 5, 2003
INVENTOR(S) : John M. Kelly et al.

It is certified that error appears in the above-identified patent and that said Letters Patent is hereby corrected as shown below:

Column 14, Line 16: "3,3,5-Tetraetthylcyclohexylmethyl amine" should be -- 3,3,5,5-Tetramethylcyclohexylmethylamine --.

Signed and Sealed this

Twenty Second Day of April, 2008

JON W. DUDAS
*Director of the United States Patent and Trademark Office*